United States Patent [19]

Kato et al.

[11] Patent Number: 4,866,055
[45] Date of Patent: * Sep. 12, 1989

[54] CEPHALOSPORIN DERIVATIVES AND THEIR CRYSTALLINE DERIVATIVES

[75] Inventors: Kazuo Kato, Mishima; Kimihiro Murakami; Hidenori Mochizuki, both of Gotenba; Ei Mochida, Toshima, all of Japan

[73] Assignee: Mochida Pharmaceutical Co., Ltd., Tokyo, Japan

[*] Notice: The portion of the term of this patent subsequent to Jun. 20, 2006 has been disclaimed.

[21] Appl. No.: 120,932

[22] Filed: Nov. 16, 1987

[30] Foreign Application Priority Data

Nov. 25, 1986 [JP] Japan .................. 61-280019

[51] Int. Cl.$^4$ .................. C07D 501/36; A61K 31/545
[52] U.S. Cl. .................................. 514/206; 540/226; 540/227
[58] Field of Search .................. 514/206; 540/226, 227

[56] References Cited

U.S. PATENT DOCUMENTS

| | | | |
|---|---|---|---|
| 4,103,085 | 7/1978 | Naito et al. | 544/27 |
| 4,104,469 | 8/1978 | Naito et al. | 544/27 |
| 4,151,352 | 4/1979 | Naito et al. | 544/26 |
| 4,278,793 | 7/1981 | Durckheimer et al. | 544/27 |
| 4,316,024 | 2/1982 | Iimura et al. | 548/27 |
| 4,331,666 | 5/1982 | Nannini et al. | 424/246 |
| 4,436,912 | 3/1984 | Wheeler | 548/233 |
| 4,500,526 | 2/1985 | Imae et al. | 514/226 |
| 4,526,977 | 7/1985 | Commons et al. | 548/246 |
| 4,547,494 | 10/1985 | Oine et al. | 514/204 |
| 4,576,956 | 3/1986 | Makisumi | 514/380 |
| 4,587,333 | 5/1986 | Ono et al. | 544/21 |
| 4,594,417 | 6/1986 | Yang | 544/28 |
| 4,600,773 | 7/1986 | Engel | 544/30 |
| 4,604,457 | 8/1986 | Torii et al. | 540/223 |
| 4,609,654 | 9/1986 | Labeeuw et al. | 514/206 |
| 4,621,081 | 11/1986 | O'Callaghan et al. | 514/206 |

FOREIGN PATENT DOCUMENTS

| | | |
|---|---|---|
| 75805 | 4/1983 | European Pat. Off. . |
| 150507 | 8/1985 | European Pat. Off. . |
| 2128498 | 12/1971 | Fed. Rep. of Germany . |
| 2456109 | 12/1980 | France . |
| 60-142987 | 7/1985 | Japan . |
| 61-126089 | 6/1986 | Japan . |
| 189245 | 1/1977 | New Zealand . |
| 203436 | 6/1980 | New Zealand . |
| 186968 | 4/1981 | New Zealand . |
| 188163 | 10/1981 | New Zealand . |
| 196642 | 7/1984 | New Zealand . |
| 202332 | 10/1985 | New Zealand . |
| 206704 | 4/1986 | New Zealand . |
| WO86/05786 | 10/1986 | PCT Int'l Appl. . |
| 893428 | 4/1962 | United Kingdom . |
| 1399086 | 6/1975 | United Kingdom . |
| 2017702A | 10/1979 | United Kingdom . |
| 1576625 | 10/1980 | United Kingdom . |
| 1604971 | 12/1981 | United Kingdom . |
| 2104888A | 3/1983 | United Kingdom . |

OTHER PUBLICATIONS

J. Antibiotics 36; 532, 1983, T. Nakagome et al.
J. Antibiotics 37; 532, 1984, T. Kamiya et al.
J. Antibiotics 39; 1236, 1243, 1986, M. Arimoto et al.
Chem. Abstracts 102:113169e.
Dunn, J. Antimicrob Chemotheraph (1982) 10 Suppl. C, pp. 1–10.
Naito et al., "Cephalosporins III," 30 Journal of Antibiotics 705 (9/77).
Alpegian et al., Cephalosporins VI, 36 Journal of Antibiotics, pp. 1013–1019 (August 1983).
Chemical Abstracts, vol. 103, 1985, Abstract No. 37281p.
Chemical Abstracts vol. 100, 1984, Abstract No. 22505d.
Chemical Abstracts, vol. 102, 1985, Abstract No. 6056u.
Chemical Abstracts, vol. 102, 1985, Abstract No. 24539z.

*Primary Examiner*—Nicholas S. Rizzo
*Attorney, Agent, or Firm*—Oliff & Berridge

[57] ABSTRACT

The present invention relates to novel cephalosporin derivatives and their crystalline form, processes for preparing thereof, compositions for treating and/or preventing infectious diseases which comprise the novel cephalosporin derivatives as active components, and the intermediate compounds in the synthesis of cephalosporin derivatives and processes for producing thereof.

The present invention is based on the selection of a triazolopyrimidine ring as substituent at the 3-position of the cephem skeleton, and a 2-carboxy-4,5-dihydroxyphenylmethyloxyimino moiety as substituent at the 7-position of the cephem skeleton.

The compounds of the present invention containing these substituents have a wide antibacterial spectrum against Gram-negative bacteria including *Pseudomonas aeruginosa* and Gram-positive bacteria including methicillin-resistant *Staphylococcus aureus*. These compounds are extremely useful for the treatment of infectious diseases.

13 Claims, No Drawings

CEPHALOSPORIN DERIVATIVES AND THEIR CRYSTALLINE DERIVATIVES

BACKGROUND OF THE INVENTION

The present invention relates to novel cephalosporin derivatives and their crystalline form, processes for producing them, and to pharmaceutical compositions containing them for treating and/or preventing infectious diseases.

Developments of cephalosporin derivatives have been remarkable. Some cephalosporin derivatives have been developed which have excellent antibacterial activity against Gram-negative bacteria including *Pseudomonas aeruginosa*. However, the antibacterial activity of these cephalosporin derivatives is rather poor against Gram-positive bacteria. Several cephalosporin antibiotics have been used for the treatment of Gram-positive bacteria infections and the increase of Gram-positive bacteria resistant to cephalosporin antibiotics, for example, methicillin-resistant *Staphylococcus aureus* (MRSA), has become widely known year by year.

From the foregoing background, it has been desired to develop cephalosporin derivatives having a strong antibacterial activity against Gram-positive bacteria while retaining a sufficient antibacterial activity against Gram-negative bacteria including *Pseudomonas aeruginosa*.

SUMMARY OF THE INVENTION

An object of the present invention is to provide novel cephalosporin derivatives and salts, solvates, salts of solvates thereof and crystalline form of them.

Another object of the present invention is to provide processes for producing novel cephalosporin derivatives and their crystalline form.

A further object of the present invention is to provide compositions for preventing and/or treating infectious diseases which comprise novel cephalosporin derivatives as active components.

A further object of the present invention is to provide intermediate compounds in the synthesis of cephalosporin derivatives and processes for producing such intermediate compounds.

The present invention is based on the selection of a triazolopyrimidine ring as substituent at the 3-position of the cephem skeleton, and a 2-carboxy-4,5-dihydroxyphenylmethyloxyimino moiety as substituent at the 7-position of the cephem skeleton. The compounds of the present invention containing these substituents have a wide antibacterial spectrum against Gram-negative bacteria including *Pseudomonas aeruginosa* and Gram-positive bacteria including methicillin-resistant *Staphylococcus aureus*. These compounds are extremely useful for the treatment of infectious diseases.

The trisodium salt of the compounds of the present invention is generally an amorphous solid and possesses an excellent solubility which is strongly required for parenteral use. But the stability of the salt is not necessarily sufficient for the pharmaceutical uses as bulk materials or as parenteral preparations. As a result of extensive studies to improve the stability of the compounds, the present inventors have now discovered that highly pure and stable crystalline form of the compounds of the present invention can advantageously and consistently be prepared and isolated.

DETAILED DESCRIPTION OF THE INVENTION

As a result of extensive investigations concerning development of cephalosporin derivatives having a satisfactory antibacterial activity against negative bacteria including *Pseudomonas aeruginosa* and also having strong antibacterial activity against Gram-positive bacteria, the present inventors have found that cephalosporin derivatives represented by the general formula (I) as shown below satisfy these requirements and, have accomplished the present invention.

The present invention is based on the selection of a triazolopyrimidine ring as substituents at the 3-position of the cephem skeleton, and of a 2-carboxy-4,5-dihydroxyphenylmethyloxyimino moiety as substituents at the 7-position of the cephem skeleton.

The present invention is directed to cephalosporin derivatives represented by the general formula (I):

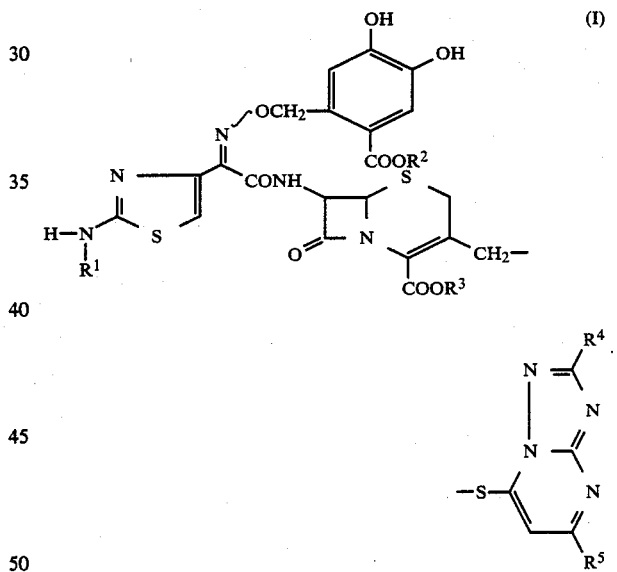

and salts, solvates and salts of solvates thereof; wherein $R^1$ represents a hydrogen atom or an amino-protecting group, $R^2$ and $R^3$ independently represent a hydrogen atom or a carboxy-protecting group, $R^4$ represents a hydrogen atom, a hydroxy group, an amino group, a sulfo group, a carboxy group or a protected carboxy group, $R^5$ represents a hydrogen atom, a methyl group, a carboxy group, a protected carboxy group, a carboxymethyl group or a protected carboxymethyl group, and the bond shown with a wavy line represents a bond of anti-form or syn-form.

The present invention ion is also directed to crystalline form of a cephalosporin derivative represented by the formula (I'):

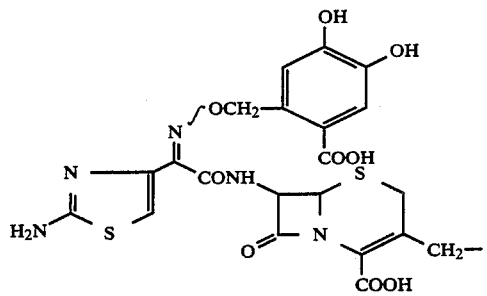

(I')

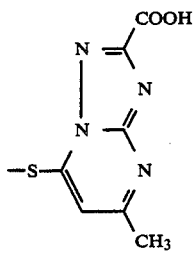

and salts, solvates especially hydrates and salts of solvates thereof.

The present invention is also directed to the processes for preparing above-mentioned cephalosporin derivatives and their crystalline form. The present invention is further directed to pharmaceutical compositions for treating and/or preventing infectious diseases characterized by containing these cephalosporin derivatives as active components.

In the cephalosporin derivatives of the present invention represented by the general formula (I), it is known that the aminothiazole moiety as the substituent at the 7-position thereof exhibits tautomerism as shown below:

sium salts, etc.), alkaline earth metal salts (calcium salts, etc.), salts of organic bases (ammonium salts, benzylamine salts, diethylamine salts, etc.), and salts of amino acids (arginine salts, lysine salts, etc.). These salts of the compounds may be mono-salts, di-salts or tri-salts. In the case of mono-salts or di-salts, the salts may be salts of the carboxy group at the 2-position and/or salts of the carboxy or sulfo group contained in the substituents at the 3-position, and/or salts of the carboxy group in the acyl group at the 7-position, of the cephem skeleton. Typical examples of acid addition salts of the compounds represented by the general formula (I) include pharmaceutically acceptable salts, such as salts of inorganic acids (hydrochlorides, hydrobromides, sulfates, phosphates, etc.), salts of organic acids (acetates, citrates, maleates, tartarates, benzoates, ascorbates, ethanesulfonates, toluenesulfonates, etc.), and salts of amino acids (aspartates, glutamates, etc.). These salts of the compounds may be monosalts or di-salts. In the case of mono-salts, the salts may form in the aminothiazole ring as substituent at the 7-position of the cephem skeleton or in the triazolopyrimidine ring as substituent at the 3-position of the cephem skeleton.

The compounds represented by the general formula (I) may form solvates especially formic acid solvates or hydrates.

The compounds of the present invention represented by the general formula (I) may be present as a syn-isomer shown below:

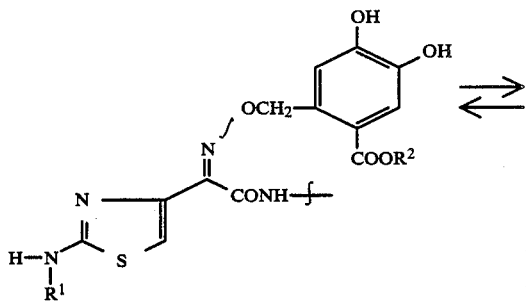

wherein $R^1$, $R^2$ and the bond shown with a wavy line have the same significance as defined above. In the present invention, the aminothiazole moiety is expressed as including both isomers since both are generally deemed to be the same substance. Accordingly, the compounds of the present invention represented by the general formula (I) also include both of these tautomeric isomers.

The compounds represented by the general formula (I) may form base or acid addition salts. Typical examples of base salts of the compounds represented by the general formula (I) include pharmaceutically acceptable salts such as alkali metal salts (sodium salts, potas-

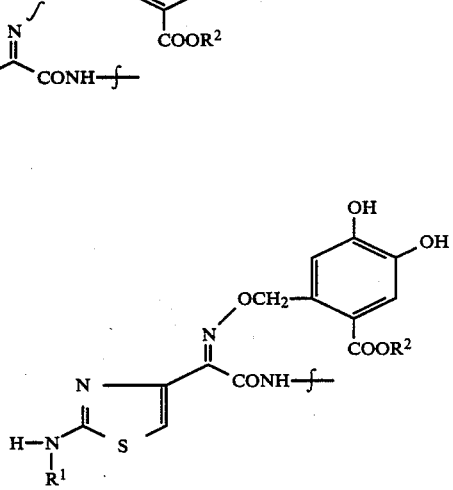

wherein $R^1$ and $R^2$ have the same significance as defined above; or as an anti-isomer shown below:

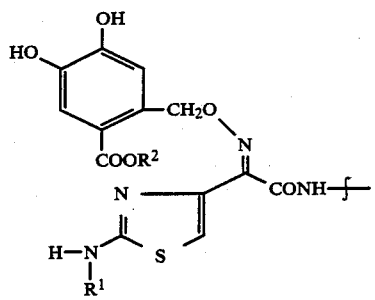

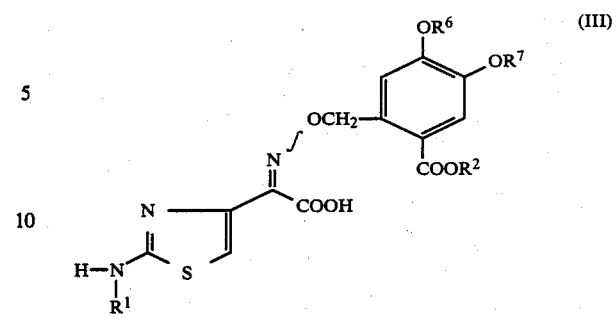

wherein $R^1$ and $R^2$ have the same significance as defined above; or as a mixture of these isomers. Among them, the syn-isomer is particularly preferred and, mixtures mainly composed of the syn-isomer are also preferred.

In the compounds of the present invention represented by the general formula (I), the amino-protecting groups may be selected from acyl groups such as formyl, acetyl, chloroacetyl, t-butoxycarbonyl, benzyloxycarbonyl, etc.; or aralkyl groups such as benzyl, diphenylmethyl, triphenylmethyl, etc. Trimethylsilyl group may also be used as an amino-protecting group. The carboxy-protecting groups may be selected from alkyl esters such as methyl ester, ethyl ester, t-butyl ester, etc.; or aralkyl esters such as benzyl ester, diphenylmethyl ester, triphenylmethyl ester, etc.; or trialkylsilyl esters such as trimethylsilyl ester, etc. Inorganic or organic bases may also be used as carboxy-protecting groups. Collectively taking account of various operations, synthesis of thus protected products, and conditions for the removal of protecting groups, it is preferred to use a triphenylmethyl group as the amino-protecting group and a diphenylmethyl group as the carboxy-protecting group.

The compounds of the present invention represented by the general formula (I) can be produced as follows. Namely;

Process A

The compounds of the present invention represented by the general formula (I) can be produced by reacting compounds represented by the general formula (II):

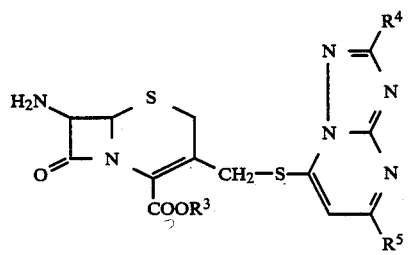

wherein $R^3$, $R^4$ and $R^5$ have the same significance as defined above, with compounds represented by the general formula (III):

wherein $R^1$, $R^2$ and the bond shown with a wavy line have the same significance as defined above, and $R^6$ and $R^7$ are the same or different and independently represent a hydrogen atom or a hydroxy-protecting group or together represent a isopropylidene group.

If necessary and desired, the compounds represented by the general formula (II) may be converted into reactive derivatives at the amino group thereof.

The compounds represented by the general formula (II) may be reacted with the compounds represented by the general formula (III) using suitable condensing agents, such as N,N'-dicyclohexylcarbodiimide, N-ethyl-5-phenylisoxazolium-3'-sulfonate, etc. Alternatively, the compounds represented by the general formula (III) may be converted into appropriate reactive derivatives prior to the reaction with the compounds represented by the general formula (II). The appropriate reactive derivatives may be, for example, acid halides (acid chlorides, etc.), azides, acid anhydrides, particularly mixed acid anhydride with strong acids, active esters (N-hydroxysuccinimide ester, etc.) or active amides (imidazolide, triazolide, etc.).

The reaction between the compounds represented by the general formula (II) and the compounds represented by the general formula (III) may be carried out by the general formula (III) may be carried out generally in an inert organic solvent such as dioxane, tetrahydrofuran, acetonitrile, chloroform, methylene chloride, ethyl acetate, dimethylformamide, etc., if necessary and desired, in the presence of deacidifying agents. The reaction may also be carried out in an aqueous solution, preferably in the presence of deacidifying agents. As the deacidifying agents, triethylamine, diethylaniline, and the like may be used in the organic solvent system, and aqueous alkalis, preferably sodium hydroxide, sodium hydrogen carbonate, potassium carbonate, and the like may be used in the aqueous system.

The reaction may be carried out at temperatures ranging from about $-30°$ C. to room temperature, and preferably from $-10°$ C. to $10°$ C. Under the condition described above, the bond represented by a wavy line in the general formula (III) is retained.

The compounds represented by the general formula (II) used in the process of the present invention can be prepared by the method described in the Japanese Patent Kokai No. 142987 (1985). The compounds represented by the general formula (III) can generally be prepared by the methods D, E and F described below.

If necessary and desired, the protecting groups may be removed from thus obtained cephalosporin derivatives represented by the general formula (I).

Process B

The compounds represented by the general formula (I) can be produced by reacting compounds represented by the general formula (IV):

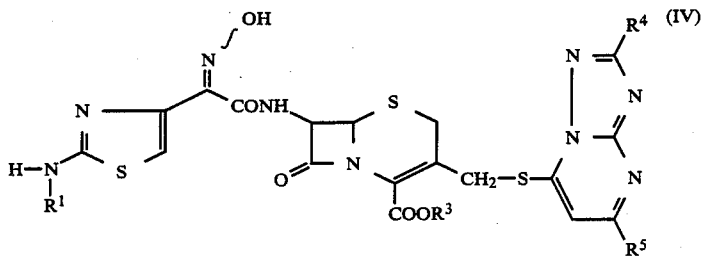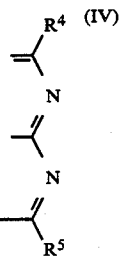

wherein $R^1$, $R^3$, $R^4$, $R^5$ and the bond shown with a wavy line have the same significance as defined above, with compounds represented by the general formula (V):

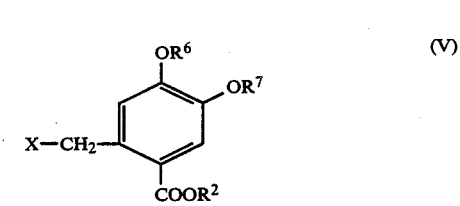

in $R^2$, $R^6$ and $R^7$ have the same significance as defined above, and X represents a halogen atom or a hydroxy group. When the compounds represented by the general formula (V) are alcohols, they may be either reacted directly with the compounds represented by the general formula (IV) in the presence of appropriate condensing agents such as triphenylphosphine or diethyl azodicarboxylate, or converted into appropriate reactive derivatives such as tosylate and then reacted with the compounds represented by the general formula (IV). However, with regard to reactivity and operability, halides are preferred for the compounds represented by the general formula (V) to be reacted with the compounds represented by the general formula (IV).

The reaction between the compounds represented by the general formula (IV) and the compounds represented by the general formula (V) may be carried out in an inert organic solvent such as dioxane, tetrahydrofuran, acetonitrile, chloroform, methylene chloride, ethyl acetate, dimethylformamide, etc. or mixture thereof, or, if necessary and desired, in water or mixture of water and organic solvents, preferably in the presence of de-acidifying agents. As the deacidifying agents, triethylamine, diethylaniline and the like may be used in organic solvents, and aqueous alkalis, preferably sodium hydroxide, sodium hydrogen carbonate, potassium carbonate and the like may be used in aqueous solvents. The reaction between the compounds represented by the general formula (IV) and the compounds represented by the general formula (V) may be carried out at temperatures ranging from about $-30°$ C. to room temperature, and preferably from $-10°$ C. to $10°$ C.

Under the condition described above, the bond represented by a wavy line in the general formula (IV) is retained. The compounds represented by the general formula (IV) can be prepared by the method described in the Japanese Patent Application No. 249193 (1984) The compounds represented by the general formula (V), in the case of halide form, can be prepared from 4-methylcatechol by the following procedure; firstly, protection of the hydroxy groups, then halogenation of the 5-position by a conventional method, then replacement of the halogen atom with a carboxyl group, then protection of the carboxyl group by esterification, and finally halogenation of the benzyl terminus by a conventional method. Then, if necessary and desired, the resultant halides can be hydrolyzed to give hydroxy form of the compounds represented by the general formula (V).

If necessary and desired, the protecting groups may be removed from thus obtained cephalosporin derivatives represented by the general formula (I).

Process C

The compounds represented by the general formula (I) can be produced by reacting compounds represented by the general formula (VI)

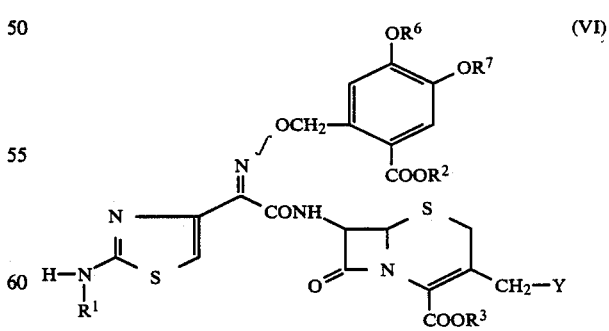

wherein $R^1$, $R^2$, $R^3$, $R^6$, $R^7$ and the bond shown with a wavy line have the same significance as defined above, and Y represents an acetoxy group or a halogen atom, with compounds represented by the general formula (VII)

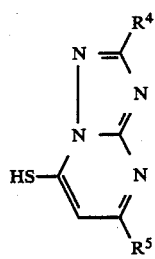

(VII)

wherein $R^4$ and $R^5$ have the same significance as defined above. The reaction can be carried out by reacting the compounds represented by the general formula (VI) with the compounds represented by the general formula (VII) in an organic solvent such as alcohols, dimethylformamide, acetonitrile, etc. or mixture thereof, or in an aqueous system. The reaction of the compounds represented by the general formula (IV) and the compounds represented by the general formula (V) may be carried out in an organic solvent, preferably in the presence of Lewis acid, such as boron trifluoride-ether complex and the like, or in an aqueous system in the presence of an appropriate amount of aqueous alkali, such as sodium hydrogen carbonate or potassium carbonate, preferably in a buffer solution at a pH in the range of 6.0 to 7.8, at temperatures in the range of about 40° C. to about 80° C., preferably at from 55° to 65° C. Under the condition described above, the bond represented by a wavy line in the general formula (VI) is retained. The compounds represented by the general formula (VI) can be prepared from the compounds represented by the general formula (III) and known 7-aminocephalosporanic acids or derivatives thereof by conventional condensation reaction. The compounds represented by the general formula (VII) can be prepared by the method described in the Japanese Patent Kokai No. 142987 (1985).

If necessary and desired, the protecting groups may be removed from thus obtained cephalosporin derivatives represented by the general formula (I).

The compounds represented by the general formula (III):

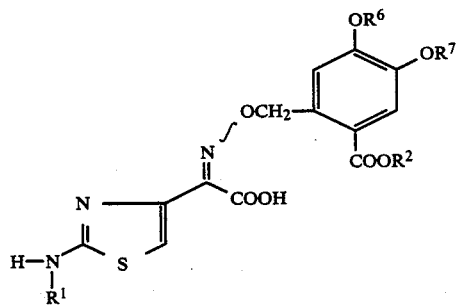

(III)

wherein $R^1$, $R^2$, $R^6$, $R^7$ and the bond shown with a wavy line have the same significance as defined above, can conveniently be prepared from the compounds represented by the general formula (VIII)

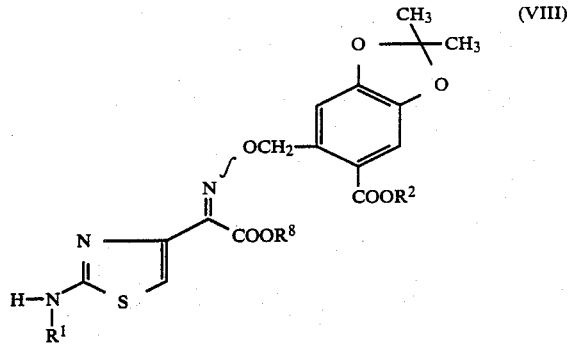

(VIII)

wherein $R^1$, $R^2$ and the bond shown with a wavy line have the same significance as defined above, and $R^8$ represents a hydrogen atom or a carboxy-protecting group.

The compounds represented by the general formula (VIII) can generally prepared by the methods described below.

Process D

The compounds represented by the general formula (VIII) can be produced by reacting the known compounds represented by the general formula (IX):

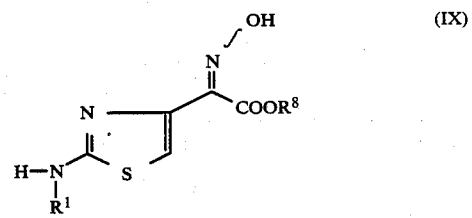

(IX)

wherein $R^1$, $R^8$ and the bond shown with a wavy line have the same significance as defined above, with the compounds represented by the general formula (V′):

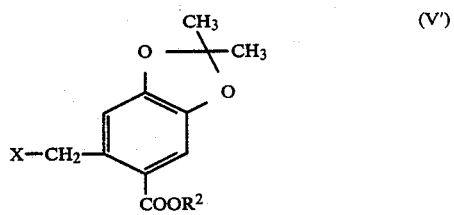

(V′)

wherein $R^2$ and X have the same significance as defined above. When the compounds represented by the general formula (V′) are alcohols, they may be either reacted directly with the compounds represented by the general formula (IX) in the presence of appropriate condensing agents such as triphenylphosphine or ethyl azodicarboxylate, or converted into appropriate reactive derivatives such as tosylate and then reacted with the compounds represented by the general formula (IX). However, with regard to reactivity and operability, halides are preferred for the compounds represented by the general formula (V′) to be reacted with the compounds represented by the general formula (IX).

The reaction between the compounds represented by the general formula (IX) and the compounds represented by the general formula (V') may be carried out in an inert organic solvent such as dioxane, tetrahydrofuran, acetonitrile, chloroform, methylene chloride, ethyl acetate, dimethylformamide, etc. or mixture thereof, or, if necessary and desired, in water or mixture of water and organic solvents, preferably in the presence of deacidifying agents. As the deacidifying agents, triethylamine, diethylaniline and the like may be used in organic solvents, and aqueous alkalis, preferably sodium hydroxide, sodium hydrogen carbonate, potassium carbonate and the like may be used in aqueous solvents.

The reaction between the compounds represented by the general formula (IX) and the compounds represented by the general formula (V') may be carried out at temperatures ranging from about −30° C. to room temperature, and preferably from −10° C. to 10° C. Under the condition described above, the bond represented by a wavy line in the general formula (IX) is retained.

The compounds represented by the general formula (V') can be prepared from 2,2,6-trimethylbenzodioxol by the method described above for the compounds represented by the general formula (V).

If necessary and desired, the protecting groups may be removed from thus obtained compounds represented by the general formula (VIII).

Process E

The compounds represented by the general formula (VIII) can be prepared by reacting the known compounds represented by the general formula (X):

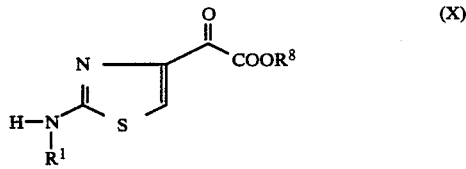

wherein $R^1$ and $R^8$ have the same significance as defined above, with the compounds represented by the formula (XI):

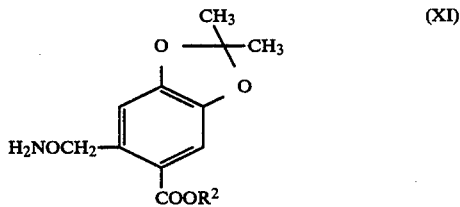

wherein $R^2$ has the same significance as defined above, in an organic solvents, such as methanol, ethanol, dioxane, tetrahydrofuran, methylene chloride and ethyl acetate, and if necessary and desired, in the presence of dehydrating agents such as molecular sieve, at temperatures in the range of from about −30° C. to about 100° C., preferably from −10° C. to 30° C.

The compounds represented by the general formula (XI) can be prepared from a halide form of the above-mentioned compounds represented by the general formula (V') by phthalimidoxylation followed by dephthaloylation, both of which can be carried out conventional methods.

If necessary and desired, the protecting groups may be removed from thus obtained compounds represented by the general formula (VIII).

Process F

The compounds represented by the general formula (VIII) can be prepared by reacting the known compounds represented by the general formula (XII):

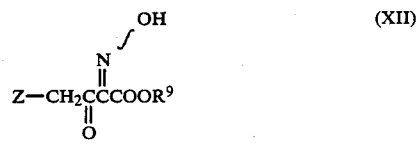

wherein $R^9$ represents a hydrogen atom or a carboxy-protecting group, and Z represents a halogen atom, with the compounds represented by the general formula (V'):

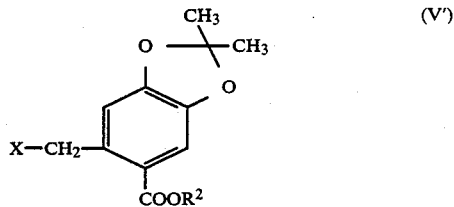

wherein $R^2$ and X have the same significance as defined above, by the method same as above-mentioned process D, then by condensing the product with the thiourea derivatives represented by the general formula (XIII):

wherein $R^1$ have the same significance as defined above. Under the condition described above, the bond represented by a wavy line in the general formula (XII) is retained. With regard to reactivity and operability, it is desirable to react an alcohol form of the compounds represented by the general formula (V') with the compounds represented by the general formula (XII).

In the present process, the condensation with the thiourea-derivatives can be carried out in an organic solvent such as methanol, ethanol, dioxane, tetrahydrofuran, methylene chloride and ethyl acetate, or mixture thereof, and preferably in the presence of deacidifying agent such as triethylamine, diethylaniline, sodium hydrogen carbonate and potassium carbonate, at temperatures in the range of from about −30° C. to about 100° C., preferably from −10° C. to 30° C.

If necessary and desired, the protecting groups may be removed from thus obtained compounds represented by the general formula (VIII).

The trisodium salt of the compound of the present invention represented by the formula (I') is generally an amorphous solid. The salt possesses an excellent solubility which is strongly required for parenteral use, but the stability of the salt is not necessarily sufficient for the pharmaceutical use as bulk materials or as parenteral preparations. As a result of extensive studies to improve the stability of the compound, the present inventors have now discovered that highly pure crystalline compound of the present invention represented by the formula (I'), (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)-thiomethyl-8-oxo-5-thia-1-azabicyclo[4.2.0]oct-2-ene-2-carboxylic acid, can advantageously and consistently be prepared and isolated. In particular, the present inventors have prepared and isolated crystalline hydrated (6R,7R)-7-[2-(2-amino-4-thiazol-yl)-2-[Z-[(2-carboxy-4,5-dihydroxyphenyl)methyl]oxyimino] acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid. This new crystalline hydrated compound is superior not only in its crystallinity and increased purity but is also obtained in high yields and has increased stability on storage. These properties of the crystalline material render it of particular value in pharmaceutical use.

The above hydrated crystalline material was characterized by its infrared spectrum and for X-ray powder diffraction pattern.

IR spectrum (Nujol : $\nu_{max}$ 3600–2200, 3275, 1769, 1652, 1596, 1542, 1521, 1519, 1307, 1272, 1190, 1160, 1103, 1064, 1026, 964, 901, 854, 795, 770 cm$^1$. X-ray diffraction pattern [given as d spacings in ÅAngström units and percentage intensities]:

| d (Å) | I (%) | d (Å) | I (%) |
|---|---|---|---|
| 19.11 | 55 | 3.79 | 74 |
| 14.34 | 11 | 3.66 | 44 |
| 9.48 | 48 | 3.56 | 73 |
| 8.73 | 13 | 3.36 | 47 |
| 7.19 | 37 | 3.22 | 22 |
| 6.27 | 82 | 3.15 | 13 |
| 5.73 | 58 | 3.11 | 26 |
| 5.34 | 20 | 2.85 | 28 |
| 5.21 | 28 | 2.75 | 12 |
| 4.78 | 77 | 2.62 | 13 |
| 4.53 | 42 | 2.49 | 10 |
| 4.26 | 25 | 2.12 | 13 |
| 3.97 | 100 | 1.98 | 16 |

The crystalline hydrated compound represented by the formula (I') can be prepared conveniently from a solution of a solvate or a salt of the said compound. Thus, according to a further embodiment of the invention we provide a process to prepare crystalline hydrated (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]-pyrimidin-7-yl)thiomethyl]-8-oxo-5-thia-1-azabicyclo[4.2.0]oct-2-ene-2-carboxylic acid by adjusting the pH of a solvate (acetic acid solvate, formic acid solvate, etc.), an acid addition salt (trifluoroacetic acid salt, etc.) or a base salt (trisodium salt, etc.) of the said acid in an appropriate aqueous medium to a pH in the range of from 1.0 to 4.0, preferably from 1.5 to 2.5, and at a temperature in the range of from −40° C. to 80° C., preferably from 15° C. to 50° C. The adjustment of pH may be performed by the use of an inorganic acid, such as hydrochloric acid, sulfuric acid or phosphoric acid, or a mixture thereof. If necessary and desired, crystallization may be performed using a seed crystal, and recrystallization may be carried out in an appropriate acidic solvent in the conventional way. The solvent may contain water, lower aliphatic alcohols such as methanol, ethanol, isopropanol, aqueous carbonic acid, lower aliphatic carboxylic acids such as formic acid, acetic acid, organic amides such as N,N-dimethylformamide, N,N-dimethylacetamide, N-methylpyrrolidone, ethers such as monoglyme, diglyme, tetrahydrofuran, or a mixture thereof. Mixed solvents such as 50% acetone-water or 30% methanol-water may also be used. Non-toxic salts at the carboxyl groups of the compounds represented by the formula (I') may include inorganic salts such as alkali metal salts (sodium salts, potassium salts, etc.), alkaline earth metal salts (calcium salts, etc.), amino acid salts (lysine salts, arginine salts, etc.) and organic base salts (procaine salts, phenylethylbenzylamine salts, dibenzylethylenediamine salts, diethanolamine salts, N-methylglucosamine salts, etc.), most preferably sodium salts. Other non-toxic salts may include acid addition salts formed with, for example, hydrochloric acid, hydrobromic acid, sulfuric acid, nitric acid, formic acid and trifluoroacetic acid.

In the preparation of crystalline hydrated form of compound represented by the formula (I'), (6R,7R)-7--[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)-thiomethyl]-8-oxo-5-thia-1-azabicyclo[4.2.0]oct-2-ene-2-carboxylic acid, its formic acid solvate is especially preferred as the starting material. The formic acid solvate itself can also be crystallized, and the crystallized solvate as well as the method to prepare the said crystallized solvate are also included in the present invention.

The crystallized formic acid solvate of the compound represented by the formula (I') was characterized by its infrared spectrum (and for X-ray powder diffraction pattern).

IR spectrum (Nujol): $\nu_{max}$ 3600–2200, 3269, 1770, 1654, 1596, 1517, 1509, 1303, 1188, 1159, 1101, 1061, 1025, 962, 904, 853, 794, 770 cm$^1$.

X-ray diffraction pattern [given as d spacings in Ångström units and percentage intensities]:

| d (Å) | I (%) | d (Å) | I (%) |
|---|---|---|---|
| 18.87 | 39 | 3.63 | 52 |
| 10.01 | 22 | 3.51 | 88 |
| 9.17 | 22 | 3.32 | 60 |
| 8.25 | 20 | 3.12 | 48 |
| 7.54 | 23 | 3.00 | 28 |
| 6.18 | 40 | 2.76 | 32 |
| 5.71 | 22 | 2.67 | 27 |
| 5.05 | 34 | 2.52 | 32 |
| 4.77 | 41 | 2.49 | 31 |
| 4.53 | 55 | 2.47 | 29 |
| 4.24 | 42 | 2.31 | 26 |
| 3.97 | 57 | 2.23 | 25 |
| 3.77 | 100 | 2.03 | 21 |

Crystalline formic acid solvate of (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7 yl)thiomethyl]-8-oxo-5-thia-1-azabicyclo[4,2,0]oct-2-ene-2-carboxylic acid can generally be prepared from its amorphous base salts, such as trisodium salts, or from acid addition salts, such as hydrochloric acid salts or trifluoroacetic acid salts. Thus, corresponding cephalosporin derivative or its salt can efficiently be crystallized from formic acid at a temperature in the range of from 0° C. to 60° C., preferably from 15° C. to 50° C., and if necessary and desired, using acids such as hydrochloric acid. The crystallization may also be facilitated by adding water to the solution, or the use of seed crystals.

The compounds of the present invention show a potent antibacterial activity against a wide range of bacteria including Gram-positive and Gram-negative bacteria, especially against methicillin-resistant *Staphylococcus aureus* and *Pseudomonas aeruginosa*, and are quite useful as therapeutic agents for infectious diseases.

To demonstrate the utility of the compounds of the present invention, data on antibacterial activity of a representative compound (referred to as Compound 1) are shown below. A compound described in another invention of the present inventors, Japanese Patent Application No. 147359 (1985), is used as a reference compound.

Compound 1: (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]-oct-2-ene-2-carboxylic acid Reference compound: (6R,7R)-7-[2-(2-amino-4-thiazolyl)-2-[Z-[(4-acetoxy-2-carboxy-5-hydroxyphenyl)methyl]oxyimino]acetamido]-3-[(2-caboxy-5-methyl-s-triazolo[1,5-a]pyrimidin-7-yl)thiomethyl]-8-oxo-5-thia-1-azabicyclo[4.2.0]oct-2-ene-2-carboxylic acid Experimental Example 1

Antibacterial activity in vitro was determined in accordance with the agar plate dilution method.

A platinum loop each of test bacteria ($10^6$ cells/ml), cultured in Mueller Hinton broth, was inoculated on Mueller Hinton agar plates which contained test compounds at various concentrations. After cultivating at 37° C. for 20 hours, the minimum inhibitory concentration (MIC μg/ml) was determined.

TABLE 1-a

| | MIC (μg/ml) | | |
|---|---|---|---|
| compound | Staphylococcus aureus Smith | Escherichia coli NIHJ JC 2 | Serratia marcescens IFO 3759 |
| Compound 1 | 1.56 | 0.39 | 0.10 |
| Reference compound | 1.56 | 0.39 | ≦0.05 |
| CAZ** | N.D. | 0.20 | ≦0.05 |

N.D. Not determined.
**Ceftazidime

TABLE 1-b

| | MIC (μg/ml) | | |
|---|---|---|---|
| compound | Proteus morganii IFO 3848 | Klebsiella pneumoniae IFO 3317 | Pseudomonas aeruginosa 13 |
| Compound 1 | 0.39 | ≦0.05 | 0.10 |
| Reference compound | 0.20 | ≦0.05 | 1.56 |
| CAZ** | 0.20 | ≦0.05 | 1.56 |

N.D. Not determined.
**Ceftazidime

As shown in Tables 1-a through 1-b, Compound 1 was about equipotent to the reference compound against the bacterial strains except *Pseudomonas aeruginosa*, against which Compound 1 was more than 10 times as potent as the reference compound and Ceftazidime.

Experimental Example 2

Protection ability against systemic infection was determined as follows. An aqueous suspension of test bacteria was intraperitoneally injected into 10 four week old ICR mice. One hour after the infection, test compounds were intravenously administered. The number of surviving mice was counted 1 week after injection to determine the dose at which 50% of the test animals were alive ($ED_{50}$: mg/kg).

TABLE 2-a

| | $ED_{50}$ (mg/Kg) | | |
|---|---|---|---|
| compound | Staphylococcus aureus 242 | Escherichia coli 67 | Serratia marcescens 274 |
| Compound 1 | 7.68 | 1.05 | 0.77 |
| Reference compound | 12.4 | 7.66 | 2.56 |
| CMD** | 8.94 | N.D. | N.D. |
| CAZ*** | >100 | 6.48 | 3.62 |

N.D. Not determined.
*Methicillin-resistant strain
**Cefamandole
***Ceftazidime

TABLE 2-b

| | $ED_{50}$ (mg/Kg) | | |
|---|---|---|---|
| compound | Proteus mirabilis IFO 3849 | Klebsiella pneumoniae IFO 3317 | Pseudomonas aeruginosa 13 |
| Compound 1 | 5.07 | 0.27 | 61.8 |
| Reference compound | 20.1 | 3.58 | >500 |
| CMD** | N.D. | N.D. | N.D. |
| CAZ*** | 4.36 | 10.6 | 145 |

N.D. Not determined.
**Cefamandole
***Ceftazidime

As shown in Tables 2-a through 2-b, Compound 1 was evidently more potent than the reference compound in protecting the animals from experimental infection and, especially, was more than 10 times as potent as the reference compound against infections with *Klebsiella pneumoniae* and *Pseudomonas aeruginosa*.

Next, $LD_{50}$ of representative examples of the compounds of the present invention is shown in Table 3 herein $LD_{50}$ was determined in accordance with the Probit method.

TABLE 3

| compound | LD$_{50}$ (mg/Kg, i.v.) |
| --- | --- |
| Compound 1 | >4000 |
| CAZ*** | >4000 |

***Ceftazidime

The compounds of the present invention are active against microorganisms, such as Gram-positive aerobic bacteria such as *Staphylococcus aureus, streptococci*, etc., Gram-negative aerobic bacteria such as *Escherichia coli, Klebsiella pneumoniae, Proteus mirabilis, Proteus morganii, Serratia marcescens, Pseudomonas aeruginosa, Citrobacter, Enterobacter, Flavobacter*, etc. and are useful for the treatment of infectious diseases caused by these microorganisms. The compounds of the present invention show a therapeutic efficacy against *Pseudomonas aeruginosa* infections which is more potent than those of β-lactam antibiotics ever known; these compounds are also thought to be highly safe. Therefore, the compounds of the present invention are expected to be extremely useful against Pseudomonal infections.

The cephalosporin derivatives provided by the present invention can be employed as pharmaceutical compositions, for example, in the form of pharmaceutical compositions containing cephalosporin derivatives together with appropriate, pharmaceutically acceptable carriers. The pharmaceutical composition may take a solid form, such as tablets, capsules, etc. or a liquid form, such as injections, etc. The compositions may be sterilized and may contain auxiliary agents generally employed in the pharmaceutical art, such as sodium hydrogen carbonate, citric acid, propylene glycol, Tween 80, etc.

Further, it is also preferred to use the compounds of the present invention after they are formed into freeze-dried products or powders followed by dissolving them in a conventional solvent, e.g., water or physiological saline, before use. The compounds can be used orally or parenterally. While dose varies depending upon age and conditions of the patient, conditions and kind of diseases, etc., from about 0.01 to about 10 g, preferably from about 0.1 to about 5 g, can be used as a daily dose for an adult Parenteral administration of the compounds provided by the present invention is particularly preferred.

Hereafter the present invention will be described with reference to the examples below but is not deemed to be limited thereof.

EXAMPLE 1

Preparation of (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (Compound 1)

Step 1

Preparation of 5-bromo-2,2,6-trimethylbenzodioxol

To a solution of 2,2,5-benzodioxol (21 g) in dichloromethane (160 ml) was added pyridine (12.1 ml), followed by dropwise addition of a solution of bromine (7.5 ml) under ice cooling, and the solution was stirred at room temperature for 1 hour. After removing the solvent under reduced pressure, the residue was extracted with ether (200 ml). The solution was washed thrice with water (100 ml each), twice with aqueous solution of citric acid (1N, 100 ml each), once with saturated aqueous solution of sodium hydrogen carbonate (100 ml) and once with brine (100 ml). The washed solution was dried over anhydrous sodium sulfate. The dried solution was concentrated under reduced pressure, and the residue was purified by silica gel column chromatography to give 28.4 g of the objective compound.

IR (KBr, cm$^{-1}$): 1493, 1379, 1251, 1241, 1216, 856.

NMR (CDCl$_3$, ppm): 6.9 (1H, s), 6.6 (1H, s), 2.3 (3H, s), 1.7 (6H, s)

Step 2

Preparation of 2,2,6-trimethylbenzodioxol-5-carboxylic acid

To a suspension of magnesium powder (9.64 g) in dry ether (17 ml) was slowly added a solution of the product of Step 1 (28 g) and ethyl bromide (24.8 g) in dry ether (114 ml). Addition of about 4 ml of the solution was sufficient to cause spontaneous refluxing, and the remaining portion was added dropwise over a 1.5-hour period to maintain the spontaneous reflux. After completing the dropwise addition, the reaction mixture was refluxed for additional 30 minutes, then cooled to room temperature and poured over crushed pieces of dry ice. Stirring was continued until all pieces of dry ice were lost. The resultant solution was acidified with aqueous hydrochloric acid (20%, 92 ml) under ice cooling and extracted twice with ether (100 ml each). The ether solution was washed 4 times with water (50 ml each), then extracted 5 times with ice-cooled aqueous sodium hydroxide solution (conc. 10%, 50 ml each). The exctract was acidified with 20% hydrochloric acid under ice cooling and stirring to pH 2, and the precipitated crystals were separated by filtration. The crystals thus obtained were washed, dried and recrystallized with ether-hexane (1:4) to give 10.8 g of the objective compound.

IR (KBr, cm$^{-1}$): 3000, 1682, 1498, 1259, 1210, 982.

NMR (CDCl$_3$; ppm): 7.5 (1H, s), 6.6 (1H, s), 2.6 (3H, s), 1.7 (6H, s).

Step 3

Preparation of t-butyl 2,2,6-trimethylbenzodioxol-5-carboxylate

To a suspension of the product obtained in Step 2 (10.6 g) in benzene (50 ml) were added thionyl chloride (15.5 ml) and N,N-dimethylformamide (2 drops), and the mixture was heated at 60° C. for 30 minutes. The solvent was removed under reduced pressure, and the residue was dissolved in methylene chloride (50 ml). The solution was then added dropwise to an ice-cooled mixture of t-butanol (37.6 g) and pyridine (24.6 ml), and the mixture was stirred at room temperature for 7 hours. After removing the solvent under reduced pressure, ether (200 ml) was added to the residue. The ether solution was washed twice with water (80 ml each), twice with aqueous hydrochloric acid (1N, 80 ml each), once with saturated aqueous solution of sodium hydrogen carbonate (80 ml) and once with brine, and the washed solution was dried over anhydrous sodium sulfate. The dried solution was concentrated under educed pressure, and the residue was purified by silica gel column chromatography to give 11.2 g of the objective compound.

IR (KBr, cm$^{-1}$). 2979, 1713, 1498, 1375, 1253, 1165.

NMR CDCl$_3$; ppm): 7.3 (1H, s), 6.6 (1H, s), 2.5 (3H, s), 1.7 (6H, s), 1.6 (9H, s).

Step 4

Preparation of t-butyl 6-bromomethyl-2,2-dimethylbenzodioxol-5-carboxylate

To a solution of the product obtained in Step 3 (11.2 g) in carbon tetrachloride (60 ml) were added N-bromosuccinimide (7.6 g) and benzoyl peroxide (30 mg) and the mixture was refluxed for 40 minutes. The reaction mixture was then cooled to room temperature and insoluble matter was removed by filtration. The filtrate was concentrated under reduced pressure, and the residue was purified by silica gel column chromatography to give 11.5 g of the objective compound.

IR (KBr, cm$^{-1}$): 2980, 1689, 1510, 1287, 1157.

NMR (CDCl$_3$; ppm): 7.3 (1H, s), 6.8 (1H, s), 4.9 (2H, s), 1.7 (6H, s), 1.6 (9H, s).

Step 5

Preparation of t-butyl 2,2-dimethyl-6-(N-phthaloyloxymethyl)benzodioxol-5-carboxylate To a solution of the product obtained in Step 4 (11.5 g) in acetonitrile (108 ml) was added dropwise a solution of N-hydroxyphthalimide (5.5 g) and triethylamine (4.7 ml) in acetonitrile (32 ml) at room temperature, and the mixture was stirred for 4 hours. The reaction mixture was poured into ice water and extracted twice with ethyl acetate (400 ml each). The organic layer was washed twice with aqueous solution of citric acid (1N, 200 ml each), 4 times with saturated aqueous solution of sodium hydrogen carbonate (200 ml each) and twice with brine (200 ml). The washed solution was dried over anhydrous sodium sulfate. The dried solution was concentrated under reduced pressure, and the residue was purified by silica gel column chromatography to give 11.2 g of the objective compound.

IR (KBr, cm$^{-1}$): 2990, 1735, 1499, 1264, 1162, 981, 701.

NMR (CDCl$_3$, ppm): 7.8 (4H, m), 7.3 (1H, s), 7.2 (1H, s), 5.6 (2H, s), 1.7 (6H, s), 1.5 (9H, s).

Step 6

Preparation of t-butyl 6-aminooxymethyl-2,2-dimethylbenzodioxol-5-carboxylate

To a solution of the product obtained in Step 5 (11.1 g) in methylene chloride (180 ml) and the solution was cooled to −30° C. To the cold solution was added a solution of methylhydrazine (1.4 ml) in methylene chloride (20 ml), and the mixture was stirred for 1 hour with ice cooling. Methylhydrazine (0.3 ml) was added again to the mixture and stirring was continued for 30 minutes. Insoluble matter was filtered off, and the filtrate was concentrated under reduced pressure. The residue was purified by silica gel column chromatography to give 7.6 g of the objective compound.

IR (KBr, cm$^{-1}$): 3530, 2990, 1703, 1498, 1252, 1160.

NMR (CDCl$_3$, ppm): 7.3 (1H, s), 6.9 (1H, s), 5.7–4.8 (2H, bs), 5.3 (2H, s), 1.7 (6H, s), 1.6 (9H, s).

Step 7

Preparation of 2-(2-amino-4-thiazolyl)-2-[Z-[(5-t-butoxycarbonyl-2,2-dimethylbenzodioxol-6-yl)methyl]oxyimino]acetic acid To a solution of the product obtained in Step 6 (7.6 g) in N,N-dimethylformamide (35 ml) was added (2-aminothiazol-4-yl)glyoxylic acid (4.4 g), and the mixture was stirred at room temperature for 30 minutes. The reaction mixture was concentrated under reduced pressure, and the residue was dissolved in ethyl acetate (200 ml). The solution was washed 4 times with water (80 ml each) and once with brine (80 ml), and dried over anhydrous sodium sulfate. The dried solution was concentrated under reduced pressure, and the residue was recrystallized with ether-hexane (1:1) to give 10.2 g of the objective compound as crystals.

IR (KBr, cm$^{-1}$): 2290, 1702, 1617, 1498, 1261.

NMR (DMSO-d$_6$, ppm): 7.24 (1H, s), 7.2 (2H, bs), 6.94 (1H, s), 6.86 (1H, s), 5.4 (2H, s), 1.7 (6H, s), 1.5 (9H, s).

Step 8

Preparation of (6R,7R)-7-[2-(2-amino-4-thiazol-yl)-2-[Z-[(5-t-butoxycarbonyl-2,2-dimethylbenzodioxol-6-yl)methyl]oxyimino]acetamido]-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester.

To a solution of the product obtained in Step 7 (3.0 g) and (6R,7R)-7-amino-3-[(2-diphenylmethyloxycarbonyl-5-methyl-s-triazolo[1,5-a]pyrimidin-7-yl)thiomethyl]-8-oxo-5-thia-1-azabicyclo[4.2.0]oct-2-ene-2-carboxylic acid diphenylmethyl ester (5.0 g) in methylene chloride (120 ml) was added N,N-dicyclohexylcarbodiimide (1.7 g), and the mixture was stirred for 12 hours at room temperature. The reaction mixture was then concentrated under reduced pressure, and the residue was dissolved in acetone (50 ml) and insoluble matter was filtered off. The filtrate was purified by silica gel column chromatography to give 5.4 g of the objective compound.

IR (KBr, cm$^{-1}$): 1791, 1700, 1498, 1377, 1223.

NMR (DMSO-d$_6$; ppm):

9.8 (1H, d, J =8 Hz), 7.6–7.1 (25H, m), 7.0 (1H, s), 6.96 (1H, s), 6.8 (1H, s), 5.9 (1H, dd, J=8, 5 Hz), 5.4 (2H, s), 5.3 1H, d, J=5 Hz) 4.3 (2H, s), 3.7 (2H, ABq), 2.6 (3H, s), 1.6 (6H, s), 1.5 (9H, s)

Step 9

Preparation of (6R,7R)-7-[2-(2-amino-4-thiazol-yl)-2-[Z-[(2-carboxy-4,5-dihydroxyphenyl)methyl]oxyimino]acetamido]-3-[(2-carboxy-5-methyl-s- triazolo[1,5-a]pyrimidin-7-yl)thiomethyl]-8-oxo-5-thia-1-azabicyclo[4.2.0]oct-2-ene-2-carboxylic acid To a suspension of the product of Step 8 (5.4 g) in dichloroethane (3.5 ml) was added anisole (3.5 g). To the mixture was added trifluoroacetic acid (14 ml) under ice cooling, and the resultant mixture was stirred at room temperature for 6 hours. The reaction mixture was then poured into ether (300 ml). The precipitated crystals were suspended in water (45 ml) and the pH of the suspension was adjusted to 8.2 with sodium hydrogen carbonate. The resultant solution was applied to a Diaion HP-20 column and eluted with water. Fractions containing the objective compound were collected and concentrated under reduced pressure. The residue was recrystallized by pouring into ethanol (70 ml) to give 1.6 g of the purified crystals.

IR (KBr, cm$^{-1}$): 1762, 1598, 1515, 1376, 1314.

NMR (D$_2$; ppm): 7.2 (1H, s), 7.1 (1H, s), 7.0 (2H, s), 5.7 (1H, d, J=5 Hz), 5.4 (2H, s), 5.1 (1H, d, J=5 Hz) 4.3 (2H, ABq), 3.5 (2H, ABq), 2.6 (3H, s).

EXAMPLE 2

Preparation of
(6R,7R)-7-[2-(2-amino-4-thiazol-yl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid Step 1

Preparation of ethyl
2-(2-amino-4-thiazolyl)-2-[Z-[(5-t-butoxycarbonyl-2,2-dimethylbenzodioxol- 6-yl)methyl]oxyimino]acetate To a solution of ethyl 2-(2-amino-4-thiazolyl-2-(Z-hydroxyimino)acetate (1 g) in dry dimethylformamide (10 ml) was added 60% aqueous solution of sodium hydride (200 mg) under ice cooling, and the mixture was stirred for 15 minutes. To the mixture was added dropwise a solution of the product obtained in Example 1, Step 4 (1.9 g) in dimethylformamide (10 ml). The mixture was stirred under ice cooling for 1.5 hours. The reaction mixture was then poured into an ice-cooled mixture of conc. hydrochloric acid and ethyl acetate (200 ml each) and stirred thoroughly. The organic layer was separated and washed once with saturated aqueous solution of sodium hydrogen carbonate (100 ml) and thrice with brine (100 ml). The washed solution was dried over anhydrous sodium sulfate. The dried solution was concentrated under reduced pressure, and the residue was recrystallized with hexane (50 ml) to give 1.85 g of the objective compound.

NMR (CDCl$_3$, ppm): 7.3 (1H, s), 6.9 (1H, s), 6.7 (1H, s), 5.7 (2H, bs), 5.6 (2H, s), 4.4 (2H, q, J=7 Hz), 1.7 (6H, s), 1.6 (9H, s), 1.4 (3H, t, J=7 Hz).

Step 2

Preparation
2-(2-amino-4-thiazolyl)-2-[Z-[(5-t-butoxycarbonyl-2,2-dimethylbenzodioxol-6-yl)-methyl]oxyimino]acetic acid To a suspension of the product of Step 1 (1 g) in ethanol (6 ml) was added an aqueous solution of sodium hydroxide (conc. 2N, 2.1 ml), and the mixture was stirred for 2 hours at room temperature then for 1 hour at 63° C. The reaction mixture was concentrated under reduced pressure, and water (20 ml) was added to the residue. The mixture was acidified with aqueous hydrochloric acid (1N) to pH 3, then extracted with ethyl acetate (50 ml). The extract was washed twice with brine (30 ml each) and dried over anhydrous sodium sulfate. The dried solution was concentrated under reduced pressure, and the residue was recrystallized with ether-hexane (1:1, 30 ml) to give 870 mg of the objective compound as crystals.

IR (KBr, cm$^{-1}$): 2290, 1702, 1617, 1498, 1261.

NMR (DMSO-d$_6$, ppm): 7.24 1H, s), 7.2 (2H, bs), 6.94 1H, s , 6.86 5.4 (2H, s), 1.7 (6H, s), 1.5 9H, s.

These data are in complete agreement with those of Step 7 of Example 1.

Step 3

Preparation of
(6R,7R)-7-[2-(2-amino-4-thiazol-yl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid The compound of the title given above was prepared from the product of Step 2, according to the methods of Steps 8 and 9 of Example 1.

IR (KBr, cm$^{-1}$): 1762, 1598, 1515, 1376, 1314.

NMR (D$_2$O; ppm): 7.2 (1H, s), 7.1 (1H, s), 7.0 (2H, s), 5.7 (1H, d, J=5 Hz), 5.4 (2H, s), 5.1 (1H, d, J=5 Hz) 4.3 (2H, ABq), 3.5 (2H, ABq), 2.6 (3H, s).

These data are in complete agreement with those of Step 9 of Example 1.

According to the method described in Example 1, compounds of Examples 3 and 4, described below, were prepared. According to the method described in Example 2, compounds of Examples 5 and 6 were prepared.

EXAMPLE 3

(6R,7R)-7-[2-(2-amino-4-thiazolyl)-2-[Z--[(2-carboxy-4,5-dihydroxyphenyl)methyl]oxyimino]acetamido]-3-[(5-methyl-s-triazolo[1,5-a]pyrimidin-7-yl)thiomethyl]-8-oxo-5-thia-1-azabicyclo[4.2.-0]oct-2-ene-2-carboxylic acid IR (KBr, cm$^{-1}$): 1762, 1595, 1514, 1380.

NMR (D$_2$O; ppm): 8.5 (1H, s), 7.2 (1H, s), 7.1 (1H, s), 7.0 (2H, s), 5.7 (1H, d, J=5 Hz), 5.4 (2H, s), 5.1 (1H, d, J=5 Hz), 4.3 (2H, ABq), 3.5 (2H, ABq), 2.6 (3H, s).

EXAMPLE 4

(6R,7R)-7-[2-(2-amino-4-thiazolyl)-2-[Z-[(2-carboxy-4,5-dihydroxyphenyl)methyl]oxyimino]acetamido]AC-ETAMIDO]-3-[(5-carboxy--triazolo[1,5-a]pyrimidin-7-yl)thiomethyl]-8-oxo-5-thia-1-azabicyclo[4.2.0]oct-2-ene-2-carboxylic acid IR (KBr, cm$^{-1}$): 1762, 1598, 1534, 1396.

NMR (D$_2$O; ppm): 8.5 (1H, s), 7.3 (1H, s), 7.1 (1H, s), 7.0 (2H, s), 5.7 (1H, d, J=5 Hz), 5.4 (2H, s), 5.1 (1H, d, J=5 Hz), 4.3 (2H, ABq), 3.5 (2H, ABq).

EXAMPLE 5

(6R,7R-[2-(2-amino-4-thiazolyl)-2-[Z-[-(2-carboxy-4,5-dihydroxyphenyl)methyl]oxyimino]acetamido]-3-[(5-carboxymethyl-s-triazolo[1,5-a]pyrimidin-7-yl)thiomethyl]-8-oxo-5-thia-1-azabicyclo[4.2.0]oct-2-ene-2-carboxylic acid IR (KBr, cm$^{-1}$): 1762, 1595, 1515, 1390

NMR (D$_2$O; ppm): 8.5 (1H, s), 7.2 (1H, s), 7.1 (1H, s), 7.0 (2H, s), 5.7 (1H, d, J=5 Hz), 5.4 (2H, s) 5.1 (1H, d, J=5 Hz), 4.3 (2H, ABq), 3.5 (2H, ABq), 2.6 (2H, s).

EXAMPLE 6

(6R,7R)-7-[2-(2-amino-4-thiazolyl)-2-[Z-[(2-carboxy-4,5-dihydroxyphenyl)methyl]oxyimino]acetamido]-3-[(2-hydroxysulfonyl-5-methyl-s-triazolo[1,5-a]pyrimidin-7-yl)thiomethyl]-8-oxo-5-thia-1-azabicyclo[4.2.0]oct-2-ene-2-carboxylic acid IR (KBr, cm$^{-1}$): 1763, 1596, 1510, 1395, 1368.

NMR (D$_2$O; ppm): 7.2 (1H, s), 7.1 (1H, s), 7.0 (2H, s), 5.7 (1H, d, J=5 Hz), 5.4 (2H, s), 5.1 (1H, d, J=5 Hz) 4.3 (2H, ABq), 3.5 (2H, ABq), 2.6 (3H, s).

EXAMPLE 7

Preparation of formic acid solvate of (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid.

Trifluoroacetic acid salt of 6R,7R-7-[2-(2-amino-4-thiazolyl)-2-[Z-[(2-carboxy-4,5-dihydroxyphenyl)methyl]oxyimino]acetamido]-3-[(2 carboxy-5-methyl-s-triazolo[1,5-a]pyrimidin-7-yl)thiomethyl]-8-oxo-5-thia-1-azabicyclo[4.2.0]oct-2-ene-2-carboxylic acid (3.0 g) was dissolved in formic acid (15 ml) at room temperature. To the solution was added water (15 ml) and the mixture was allowed to stand for 1 hour at room temperature. Additional water (5 ml) was then added and the mixture was stirred for 30 minutes at room temperature. To the mixture were added seed crystals, and stirring was continued for 1 hour. Precipitated crystals were separated by filtration, washed with water (20 ml) and dried in air to give 1.95 g of the objective compound.

IR (Nujol, cm$^{-1}$):
3600–2200, 3269, 1770, 1654, 1596, 1517, 1509, 1303, 1188, 1159, 1101, 1061, 1025, 962, 904, 853, 794, 770.

NMR DMSO-d$_6$, ppm):
9.61 (1H, d, J=8 Hz), 9.44 (1H, bs), 9.18 (1H, bs), 8.12 (s; HCOOH), 7.40 (1H, s), 7.35 (1H, s), 7.17 (2H, s), 6.89 (1H, s), 6.75 (1H, s), 5.88 (1H, dd, J=8, 4 Hz), 5.39 (2H, s), 5.20 (1H, d, J=4 Hz), 4.43 (2H, s), 3.70 (2H, ABq), 2.62 (3H, s).

X-ray diffraction pattern [given as d spacings in Ångstroöm units and percentage intensities]:

| d (Å) | I (%) | d (Å) | I (%) |
|---|---|---|---|
| 18.87 | 39 | 3.63 | 52 |
| 10.01 | 22 | 3.51 | 88 |
| 9.17 | 22 | 3.32 | 60 |
| 8.25 | 20 | 3.12 | 48 |
| 7.54 | 23 | 3.00 | 28 |
| 6.18 | 40 | 2.76 | 32 |
| 5.71 | 22 | 2.67 | 27 |
| 5.05 | 34 | 2.52 | 32 |
| 4.77 | 41 | 2.49 | 31 |
| 4.53 | 55 | 2.47 | 29 |
| 4.24 | 42 | 2.31 | 26 |
| 3.97 | 57 | 2.23 | 25 |
| 3.77 | 100 | 2.03 | 21 |

EXAMPLE 8

Preparation of formic acid solvate of (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo-[4.2.0]oct-2-ene-2-carboxylic acid.

Trisodium salt of 6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia1-azabicyclo[4.2.0]oct-2-ene-2-carboxylic acid (1.1 g) was dissolved in water (3 ml), and formic acid (1.5 ml) and water (2 ml) were added to the solution. The mixture was stirred for 5 minutes at room temperature. Additional water (5 ml) was then added and the mixture was stirred for 30 minutes at 0° C. Precipitated crystals were separated by filtration, washed with water (5 ml) and dried in air to give 0.89 g of the objective compound.

IR (Nujol, cm$^{-1}$): 3600–2200, 3255, 1764, 1701, 1653, 1597, 1542, 1517, 1305, 1268, 1220, 1203, 1186, 1172, 1157, 1103, 1065, 1020, 962, 907, 852, 795, 771.

NMR (DMSO-d$_6$, ppm):
9.61 (1H, d, J=8 Hz), 9.44 (1H, bs), 9.18(1H, bs), 8.12 (s; HCOOH), 7.40 (1H, s), 7.35 (1H, s), 7.17 (2H, s), 6.89 (1H, s), 6.75 (1H, s), 5.88 (1H, dd, J=8, 4 Hz), 5.39 (2H, s), 5.20 (1H, d, J=4 Hz), 4.43 (2H, s), 3.70 (2H, ABq), 2.62 (3H, s)

X-ray diffraction pattern [given as d spacings in Ångström units and percentage intensities]:

| d (Å) | I (%) | d (Å) | I (%) |
|---|---|---|---|
| 15.94 | 29 | 3.53 | 74 |
| 8.48 | 32 | 3.42 | 99 |
| 7.10 | 37 | 3.24 | 80 |
| 5.90 | 45 | 3.05 | 62 |
| 4.84 | 42 | 2.81 | 41 |
| 4.58 | 44 | 2.70 | 45 |
| 4.38 | 61 | 2.47 | 46 |
| 3.83 | 75 | 2.27 | 41 |
| 3.66 | 100 | 2.20 | 39 |

EXAMPLE 9

Preparation of hydrate of (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7yl)-thiomethyl[-oxo-5-thia-1-thia-1-azabicyclo oct-2-ene-2-carboxylic acid.

Trifluoroacetic acid salt of (6R,7R)-7-[2-amino-4-thiazolyl)2-[Z-[(2-carboxy-4,5-dihydroxyphenyl)methyl]acetamido]-3-[(2-carboxy-5-methyl-s-triazolo[1,5- a]pyrimidin-7-yl)thiomethyl]-8-oxo-5-thia-1-azabicyclo[4.2.0]oct-2-ene-2-carboxylic acid (3.0 g) was dissolved in formic acid (15 ml) at room temperature. To the solution was added water (15 ml) and the mixture was stirred for 1 hour at room temperature. Additional water (5 ml) was then added and the mixture was stirred for 30 minutes at room temperature. To the mixture were added seed crystals and water (10 ml), and stirring was continued for 1 hour. Precipitated crystals were separated by filtration, washed once with water (20 ml) and once by stirring in 30 ml of water, then dried in air to give 1.85 g of the objective compound.

IR (Nujol, cm$^{-1}$): 3600–2200, 3261, 1768, 1653, 1595, 1517, 1509 1305, 1269, 1188, 1158, 1103, 1063, 1024, 962, 903, 853, 795, 770.

NMR (DMSO-d$_6$, ppm):
9.54 (1H, d, J=8 Hz), 7.41 (1H, s), 7.36 (1H, s), 6.89 (1H, s), 7.4 - 6.9 (2H, bs), 6.76 (1H, s), 5.81 (1H, dd, J=8, 5 Hz), 5.39 (2H, s), 5.21 (1H, d, J=5 Hz), 4.43 (2H, bs), 4.1 (2H, bs), 2.6 (3H, s).

ray diffraction pattern [given as d spacings in Ångström units and percentage intensities]:

| d (Å) | I (%) | d (Å) | I (%) |
|---|---|---|---|
| 18.95 | 44 | 4.22 | 36 |
| 9.48 | 27 | 3.95 | 74 |
| 8.23 | 12 | 3.77 | 100 |
| 7.47 | 21 | 3.65 | 17 |
| 7.14 | 21 | 3.50 | 63 |
| 6.21 | 60 | 3.36 | 31 |
| 5.70 | 33 | 3.22 | 13 |
| 5.20 | 16 | 3.10 | 41 |
| 4.75 | 88 | 2.84 | 16 |
| 4.51 | 61 | 2.75 | 12 |

EXAMPLE 10

Preparation of hydrate of (6R,7R)-7-[2-(2-amino-4-thiazolyl)-2-[Z-[(2-carboxy-4,5-dihydroxyphenyl)methyl]oxyimino]acetamido]-3-[(3-carboxy-5-methyl-s-triazolo[1,5-a]pyrimidin-7-yl)thiomethyl]-8-oxo-5-thia-1-azabicyclo oct-2-ene-2-carboxylic acid Trisodium salt of (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl[-8-oxo-5-thia-1-azabicyclo oct-2-ene-2-carboxylic acid (1.1 g) was dissolved in water (3 ml), and formic acid (1.5 ml) was added to the solution. The mixture was stirred for 5 minutes at room temperature. Additional water 5 ml) was then added and the mixture was stirred for 30 minutes at 0° C. Precipitated crystals were separated by filtration and washed with water (once each with 2 and 1 ml). These washed crystals were redissolved in formic acid (5ml). To the solution was added water (5 ml), and the mixture was stirred for 1 hour at room temperature. Precipitated crystals were separated by filtration, washed once with water (20 ml) and once by stirring in 30 ml of water, then dried in air to give 0.89 g of the objective compound.

IR (Nujol, cm$^{-1}$):
3600–2200, 3275, 1769, 1652, 1596, 1542, 1521, 1519, 1307, 1272, 1190, 1160, 1103, 1064, 1026, 964, 901, 854, 795, 770.

NMR (DMSO-d$_6$, ppm):
9.54 (1H, d, J=8 Hz), 7.41 (1H, s), 7.36 (1H, s), 6.89 (1H, s), 7.4 - 6.9 (2H, bs), 6.76 (1H, s), 5.81 (1H, dd, J=8, 5 Hz), 5.39 (2H, s), 5.21 (1H, d, J=5 Hz), 4.43 (2H, bs), 4.1 (2H, bs), 2.6 (3H, s).

X-ray diffraction pattern [given as d spacings in Ångström units and percentage intensities]:

| d (Å) | I (%) | d (Å) | I (%) |
|---|---|---|---|
| 19.11 | 55 | 3.79 | 74 |
| 14.34 | 11 | 3.66 | 44 |
| 9.48 | 48 | 3.56 | 73 |
| 8.73 | 13 | 3.36 | 47 |
| 7.19 | 37 | 3.22 | 22 |
| 6.27 | 82 | 3.15 | 13 |
| 5.73 | 58 | 3.11 | 26 |
| 5.34 | 20 | 2.85 | 28 |
| 5.21 | 28 | 2.75 | 12 |
| 4.78 | 77 | 2.62 | 13 |
| 4.53 | 42 | 2.49 | 10 |
| 4.26 | 25 | 2.12 | 13 |
| 3.97 | 100 | 1.98 | 16 |

EXAMPLE 11

Preparation of hydrate of (6R,7R)-7-[2-(2-amino-4-thiazolyl)-2-[Z-[(2-carboxy-4,-5-dihydroxyphenyl)methyl]oxyimino]acetamido]-3-[(2-carboxy-5-methyl-s-thiazolo[1,5-a]pyrimidin-7-yl)thiomethl[-8-oxo-5-thia-1-azabicyclo oct-2-ene-2-carboxylic acid.

Formic acid solvate of (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7yl)thiomethyl]-8-oxo-5-thia-1-azabicyclo oct-2-ene-2carboxylic acid (1.85 g), obtained in either Example 7 or 8, was dissolved in formic acid (10ml). To the solution was added water (12 ml and the mixture was stirred for 30 minutes at room temperature. Additional water (10 ml) was then added and the mixture was stirred for 1 hour at room temperature. Precipitated crystals were separated by filtration, washed with water (30 ml) and dried in air to give 0.89 g of the objective compound.

IR (Nujol, cm$^{-1}$):
3600–2200, 3275, 1769, 1652, 1596, 1542, 1521, 1519, 1307, 1272, 1190, 1160, 1103, 1064, 1026, 964, 901, 854, 795, 770.

NMR DMSO-d$_6$, ppm):
9.54 (1H, d, J=8 Hz), 7.41 (1H, s), 7.36 (1H, s), 6.89 (1H, s), 7.4 - 6.9 (2H, bs), 6.76 (1H, s , 5.81 (1H, dd, J=8, 5 Hz), 5.39 (2H, s), 5.21 (1H, d, J=5 Hz), 4.43 (2H, bs), 4.1 (2H, bs), 2.6 (3H, s.

X-ray diffraction pattern [given as d spacings in Ångström units and percentage intensities]:

| d (Å) | I (%) | d (Å) | I (%) |
|---|---|---|---|
| 19.11 | 55 | 3.79 | 74 |
| 14.34 | 11 | 3.66 | 44 |
| 9.48 | 48 | 3.56 | 73 |
| 8.73 | 13 | 3.36 | 47 |
| 7.19 | 37 | 3.22 | 22 |

| d (Å) | I (%) | d (Å) | I (%) |
| --- | --- | --- | --- |
| 6.27 | 82 | 3.15 | 13 |
| 5.73 | 58 | 3.11 | 26 |
| 5.34 | 20 | 2.85 | 28 |
| 5.21 | 28 | 2.75 | 12 |
| 4.78 | 77 | 2.62 | 13 |
| 4.53 | 42 | 2.49 | 10 |
| 4.26 | 25 | 2.12 | 13 |
| 3.97 | 100 | 1.98 | 16 |

The following examples detail typical pharmaceutical preparations containing the cephalosporin derivatives of the present invention. These examples are not intended to limit the types of compounds to be used, but the methods are applicable to all the compounds of the present invention.

Example A (Method of manufacturing parenteral injections)

(6R,7R)-7-[2-(2amino-4-thiazolyl)-2-[Z(2-carboxy-4,5-dihydroxyphenyl)methyl]oxyimino]acetamido]-3-[(2-carboxy-5-methyl-s-thiazolo[1,5-a]pyrimidin-7-yl)thiomethyl[-8-oxo-5-thia-1-azabicyclo oct-2-ene-2-carboxylic acid (500 g) and 3 equivalent amounts of sodium hydrogen carbonate were uniformly mixed and distributed into 15-ml hermetic containers each weighing 500 mg by ordinary methods.

Example B (Method of manufacturing freeze-dried parenteral injections)

(6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid trisodium salt (550 g) was dissolved in 2.2 l of sterile water, and 2 ml each of this solution was poured into 10-ml ampoules, freeze-dried and sealed by ordinary methods, to produce a freeze-dried preparation for parenteral injections.

Example C (Method of manufacturing freeze-dried parenteral injections)

(6R,7R)-7-[2-(2-amino-4-thiazolyl)-2-[Z--[(2-carboxy-4,5-dihydroxyphenyl)methyl]oxyimino]acetamido]-3-[(5-methyl-s-triazolo[1,5-a]pyrimidin-7-yl)thiomethyl]-8-oxo-5-thia-1-azabicyclo[4.2.-0]oct-2-ene-2-carboxylic acid trisodium salt (500 g) was dissolved in 1.0 l of sterile water, and 2 ml each of this solution was poured into 10-ml ampoules, freeze-dried and sealed by ordinary methods, to produce a freeze-dried preparation for parenteral injections.

Example D (Method of manufacturing tablets for oral administration)

Granules were prepared by ordinary methods using 100 g of (6R,7R)-7-[2-(2-amino-4-thiazolyl)-2-[Z-[(2-carboxy-4,5-dihydroxyphenyl)methyl]oxyimino]acetamido]-3-[(5-carboxymethyl-s-triazolo[1,5-a]-pyrimidin-7-yl)thiomethyl]-8-oxo-5-thia-1-azabicyclo[4.2.0]oct-2-ene-2-carboxylic acid, 100 g of lactose, 30 g of starch, and 10 g of polyvinyl pyrrolidone. Starch (30 g) and magnesium stearate (5 g) were further added to the granules, and the resulting mixture was compressed into tablets, each piece weighing 275 mg.

Example E (Method of manufacturing gelatin capsules for oral administration)

(6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid (100 g), water-soluble polyvinyl pyrrolidone (15 g), mannitol (15 g), talc (15 g) and magnesium stearate (5 g) were uniformly mixed, and filled into gelatin capsules each weighing 150 mg.

What is claimed is:

1. A cephalosporin compound formula (I):

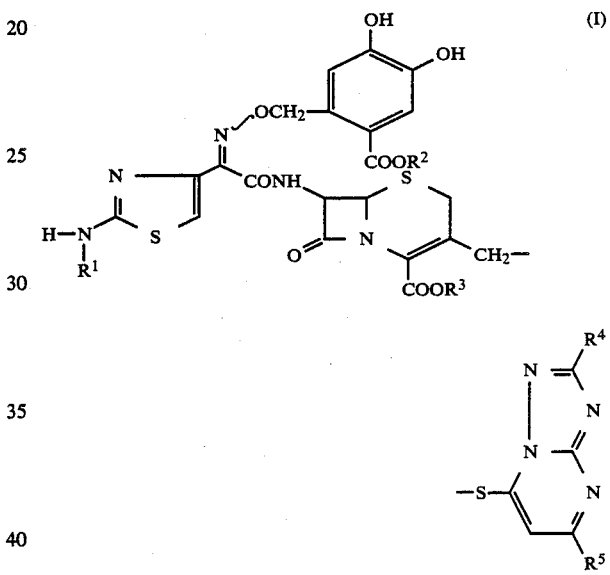

and non-toxic salts, non-toxic solvates and non-toxic salts of solvates thereof; wherein $R^1$ represents a hydrogen atom or an amino-protecting group, $R^2$ and $R^3$ are the same or different and represent hydrogen atoms or carboxy-protecting groups, $R^4$ represents a hydrogen atom, a hydroxy group, an amino group, a sulfo group, a carboxy group or a protected carboxy group, $R^5$ represents a hydrogen atom, a methyl group, a carboxy group, a protected carboxy group, a carboxymethyl group or a protected carboxymethyl group, and the bond shown with a wavy line represents a bond of anti-form or syn-form.

2. A cephalosporin compound as claimed in claim 1 wherein $R^4$ represents a carboxy group or a protected carboxy group, and $R^5$ represents a methyl group, and non-toxic salts, non-toxic solvates and non-toxic salts of solvates thereof.

3. A cephalosporin compound as claimed in claim 2 wherein the said bond shown with a wavy line represents a bond of syn-form, and non-toxic salts, non-toxic solvates and non-toxic salts of solvates thereof.

4. A compound represented by the formula (I'),

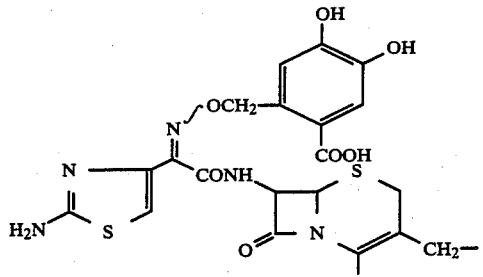

(I')

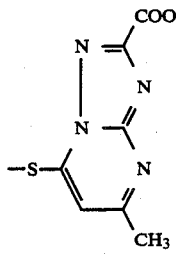

(6R,7R)-7-[2-(2-amino-4-thiazolyl)-2-[Z-[(2-carboxy-4,5-dihydroxyphenyl)methyl]oxyimino]acetamido]-3-[(2carboxy-5methyl-s-triazolo[1,5-a]pyrimidin-7-yl)thiomethyl]-8-oxo-5-thia-1-azabicyclo [4.2.0]oct-2-ene-2-carboxylic acid, and non-toxic salts, hydrates and solvates thereof.

5. Crystalline hydrate of the compound as claimed in claim 4.

6. Crystalline formic acid solvate of the compound as claimed in claim 4.

7. A compound as claimed in claim 5, which is characterized by a infrared absorption spectrum showing absorptions at 3600–2200 (broad), 3275, 1769, 1652, 1596, 1542, 1521, 1519, 1307, 1272, 1190, 1160, 1103, 1064, 1026, 964, 901, 854, 795, 770 (cm$^{-1}$, in Nujol).

8. A compound as claimed in claim 5, which is characterized by an X-ray diffraction pattern:

| d (Å) | I (%) | d (Å) | I (%) |
|-------|-------|-------|-------|
| 19.11 | 55    | 3.79  | 74    |
| 14.34 | 11    | 3.66  | 44    |
| 9.48  | 48    | 3.56  | 73    |
| 8.73  | 13    | 3.36  | 47    |
| 7.19  | 37    | 3.22  | 22    |
| 6.27  | 82    | 3.15  | 13    |
| 5.73  | 58    | 3.11  | 26    |
| 5.34  | 20    | 2.85  | 28    |
| 5.21  | 28    | 2.75  | 12    |
| 4.78  | 77    | 2.62  | 13    |
| 4.53  | 42    | 2.49  | 10    |
| 4.26  | 25    | 2.12  | 13    |
| 3.97  | 100   | 1.98  | 16    |

9. A compound as claimed in claim 6, which is characterized by a infrared absorption spectrum showing absorptions at 3600–2200 (broad), 3269, 1770, 1654, 1596, 1517, 1509, 1303, 1188, 1159, 1101, 1061, 1025, 962, 904, 853, 794, 770 (cm$^{-1}$, in Nujol).

10. A compound as claimed in claim 6, which is characterized by an X-ray diffraction pattern:

| d (Å) | I (%) | d (Å) | I (%) |
|-------|-------|-------|-------|
| 18.87 | 39    | 3.63  | 52    |
| 10.01 | 22    | 3.51  | 88    |
| 9.17  | 22    | 3.32  | 60    |
| 8.25  | 20    | 3.12  | 48    |
| 7.54  | 23    | 3.00  | 28    |
| 6.18  | 40    | 2.76  | 32    |
| 5.71  | 22    | 2.67  | 27    |
| 5.05  | 34    | 2.52  | 32    |
| 4.77  | 41    | 2.49  | 31    |
| 4.53  | 55    | 2.47  | 29    |
| 4.24  | 42    | 2.31  | 26    |
| 3.97  | 57    | 2.23  | 25    |
| 3.77  | 100   | 2.03  | 21    |

11. An antibiotic pharmaceutical composition which comprises an effective amount of one or more cephalosporin compounds represented by the formula (I):

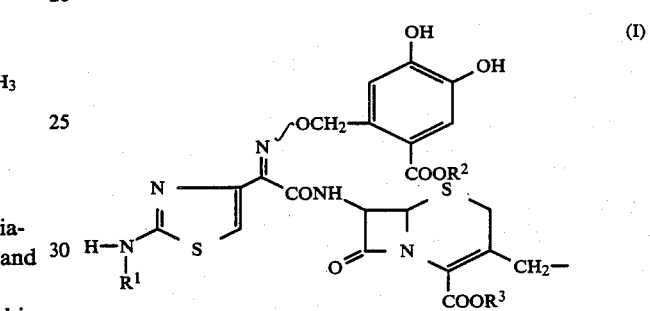

and non-toxic salts, non-toxic solvates and non-toxic salts of solvates thereof; and a pharmaceutically acceptable carrier wherein R1 represents a hydrogen atom or an amino-protecting group, $R^2$ and $R^3$ are the same or different and represent hydrogen atoms or carboxy-protecting groups, $R^4$ represents a hydrogen atom, a hydroxy group, an amino group, a sulfo group, a carboxy group or a protected carboxy group, $R^5$ represents a hydrogen atom, a methyl group, a carboxy group, a protected carboxy group, a carboxymethyl group or a protected carboxymethyl group, and the bond shown with a way line represents a bond of anti-form or syn-form.

12. The antibiotic pharmaceutical composition as claimed in claim 11 which comprises (6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl)thiomethyl]-8-oxo-5-thia-1-azabicyclo[4.2.0]oct-2-ene-2-carboxylic acid, and non-toxic salts, solvates and non-toxic salts of solvates of said cephalosporin compound.

13. An antibiotic pharmaceutical composition which comprises an effective amount of a crystalline compound represented by the formula (I'),

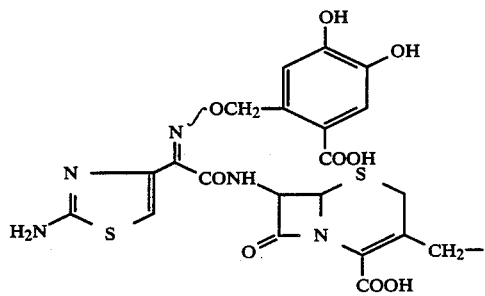

(I')

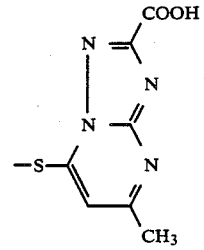

(6R,7R)-7-[2-(2-amino-4-thiazolyl)-2-[Z-[(2-carboxy-4,5-dihydroxyphenyl)methyl]oxyimino]acetamido]-3-[(2-carboxy-5-methyl-s-triazolo[1,5-a]pyrimidin-7-yl-thiomethyl]-8-oxo-5-thia-1-azabicyclo[4.2.0]oct-2-ene-2-carboxylic acid, and non-toxic salts, hydrates and solvates with a pharmaceutically acceptable carrier.

* * * * *